(12) United States Patent
Kogiso et al.

(10) Patent No.: US 8,690,899 B2
(45) Date of Patent: Apr. 8, 2014

(54) LIGATION APPARATUS

(75) Inventors: Junichi Kogiso, Hachioji (JP); Kiyotaka Matsuno, Sagamihara (JP); Mamoru Nakada, Hino (JP); Kazushi Murakami, Hino (JP)

(73) Assignees: Olympus Corporation (JP); Olympus Medical Systems Corp. (JP)

( * ) Notice: Subject to any disclaimer, the term of this patent is extended or adjusted under 35 U.S.C. 154(b) by 222 days.

(21) Appl. No.: 13/089,641

(22) Filed: Apr. 19, 2011

(65) Prior Publication Data

US 2011/0196390 A1    Aug. 11, 2011

Related U.S. Application Data

(62) Division of application No. 11/722,490, filed as application No. PCT/JP2005/023652 on Dec. 22, 2005, now Pat. No. 8,551,119.

(30) Foreign Application Priority Data

Dec. 24, 2004  (JP) .................................. 2004-374333
Aug. 10, 2005  (JP) .................................. 2005-232253

(51) Int. Cl.
*A61B 17/08*    (2006.01)

(52) U.S. Cl.
USPC ............................. 606/151; 606/142; 606/157

(58) Field of Classification Search
USPC .................. 606/139, 142, 143, 151, 157, 158
See application file for complete search history.

(56) References Cited

U.S. PATENT DOCUMENTS

| 4,085,743 | A | * | 4/1978 | Yoon | 606/140 |
| 4,226,239 | A | * | 10/1980 | Polk et al. | 606/141 |
| 5,445,167 | A | * | 8/1995 | Yoon et al. | 128/898 |
| 5,972,002 | A | * | 10/1999 | Bark et al. | 606/140 |

(Continued)

FOREIGN PATENT DOCUMENTS

| JP | 60-092510 | 5/1985 |
| JP | 63-288147 | 11/1988 |

(Continued)

OTHER PUBLICATIONS

PCT International Search Report dated Apr. 4, 2006 issued in corresponding PCT Application No. PCT/JP2005/023652.

(Continued)

*Primary Examiner* — Melanie Tyson
*Assistant Examiner* — Todd J Scherbel
(74) *Attorney, Agent, or Firm* — Ostrolenk Faber LLP

(57) ABSTRACT

A ligation apparatus that ligatures living tissue using a clip and provides an optimal ligation apparatus for ligaturing living tissue in a body cavity. The ligation apparatus includes a clip with a clip claw member that is advanced and retreated relative to a pressing member to open and close, a sheath configured to accommodate the clip such that the clip claw member is not exposed to the outside, an advance and retreat restricting mechanism which restricts advance and retreat of the pressing member relative to the sheath at a distal end portion of the sheath and allows advance and retreat of the clip claw member relative to the pressing member according to advance and retreat of the operation wire relative to the sheath to allow the clip ligaturing living tissue, and a releasing mechanism which releases at least a portion of the clip when the clip ligatures the living tissue.

6 Claims, 13 Drawing Sheets

(56) References Cited

U.S. PATENT DOCUMENTS

| | | | |
|---|---|---|---|
| 6,814,742 B2 * | 11/2004 | Kimura et al. | 606/151 |
| 8,551,119 B2 * | 10/2013 | Kogiso et al. | 606/142 |
| 2002/0045909 A1 | 4/2002 | Kimura et al. | |
| 2002/0128667 A1 * | 9/2002 | Kobayashi et al. | 606/139 |
| 2002/0138085 A1 * | 9/2002 | Muramatsu et al. | 606/139 |
| 2002/0151916 A1 * | 10/2002 | Muramatsu et al. | 606/158 |
| 2002/0177861 A1 * | 11/2002 | Sugiyama et al. | 606/151 |
| 2003/0069592 A1 * | 4/2003 | Adams et al. | 606/142 |
| 2004/0176784 A1 * | 9/2004 | Okada | 606/142 |
| 2005/0107809 A1 * | 5/2005 | Litscher et al. | 606/142 |
| 2006/0259049 A1 * | 11/2006 | Harada et al. | 606/151 |
| 2006/0271072 A1 * | 11/2006 | Hummel et al. | 606/142 |

FOREIGN PATENT DOCUMENTS

| | | | |
|---|---|---|---|
| JP | 08-126648 | | 5/1996 |
| JP | 09-289989 | | 11/1997 |
| JP | 2001-520069 | | 10/2001 |
| JP | 2003-000609 | | 1/2003 |
| JP | 2003-210471 | | 7/2003 |
| JP | 2004-121485 | | 4/2004 |
| JP | 2004-305231 | | 11/2004 |
| KR | 1984-0002156 | | 11/1984 |
| WO | WO 03/030746 | | 4/2003 |
| WO | WO2004/082488 | * | 9/2004 |
| WO | WO 2005/046489 | | 5/2005 |

OTHER PUBLICATIONS

PCT International Written Opinion dated Apr. 4, 2006 issued in corresponding PCT Application No. PCT/JP2005/023652.

International Preliminary Report on Patentability in corresponding PCT Appln. No. PCT/JP2005/023652 dated Jul. 5, 2007.

Search Report issued by European Patent Office on May 11, 2010 in connection with corresponding application No. EP 05 82 0086.

Office Action issued by the Japanese Patent Office on Jan. 11, 2011 in connection with corresponding Japanese Patent Application No. 2005-232253.

English translation of Japanese Office Action issued in connection with Japanese Patent Application No. 2005-232253 on Jan. 11, 2011.

Office Action issued by the Japanese Patent Office on Jan. 11, 2011 in connection with corresponding Japanese Patent Application No. 2008-296824.

English translation of Japanese Office Action issued in connection with Japanese Patent Application No. 2008-296824 on Jan. 11, 2011.

Untranslated Office Action issued by Korean Patent Office on Sep. 16, 2010 in connection with corresponding Korean Application No. 10-2009-7005124.

English translation of Korean Office Action dated Sep. 16, 2010 issued in connection with corresponding Korean Application No. 10-2009-7005124.

Search Report issued by European Patent Office and received by applicant on Nov. 30, 2011 in connection with corresponding EP patent application No. EP 11 00 0749.

* cited by examiner

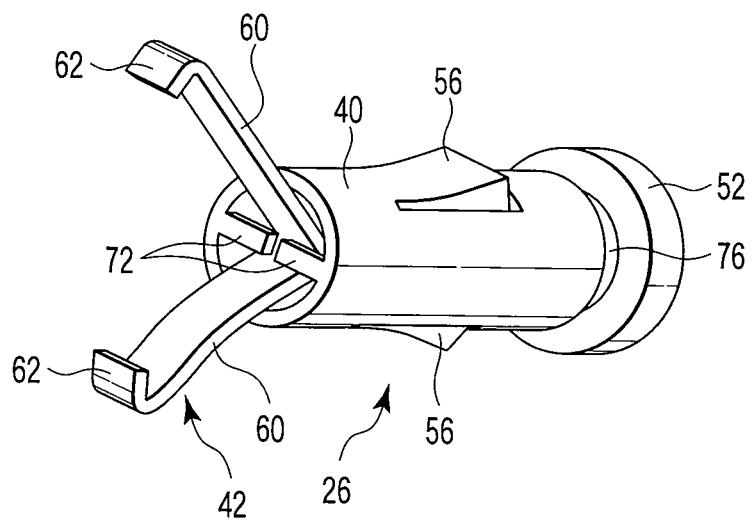
F I G. 2
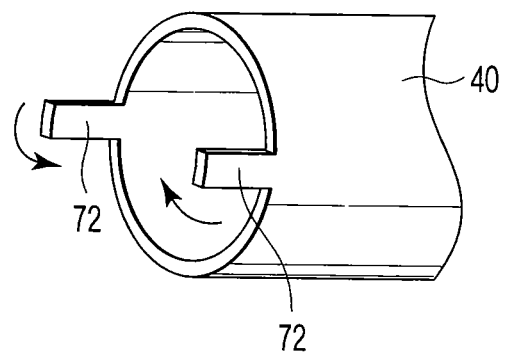
F I G. 3

LIGATION APPARATUS

CROSS REFERENCE TO RELATED APPLICATION

The present application is a Divisional of U.S. application Ser. No. 11/722,490 filed Dec. 13, 2007 which is a 35 U.S.C. §§371 national phase conversion of PCT/JP2005/023652, filed Dec. 12, 2005, which claims priority of Japanese Application No. 2004-374333, filed on Dec. 24, 2004, and Japanese Application No. 2005-232253, filed Aug. 10, 2005. The PCT International Application was published in the Japanese language.

TECHNICAL FIELD

The present invention relates to a ligation apparatus that ligatures living tissue using a clip.

BACKGROUND ART

Conventionally, a ligation apparatus that ligatures living tissue in a body cavity by a clip is used in combination with an endoscope.

In a ligation apparatus described in Jpn. Pat. Appln. KOKAI Publication No. 2004-121485, a clip includes a pair of arms biased so as to be expanded. Living tissue is grasped by fitting a pressing pipe on the clip to close the pair of arms, and the living tissue is ligatured by maintaining the pair of arms in a closed state by the pressing pipe.

In a ligation apparatus described in International Publication No. 03/030746A1 Pamphlet, a clip including a pair of clip leg portions configured to open and close is connected to a distal end portion of a coil sheath. Living tissue is grasped by withdrawing a proximal end portion of the clip leg portions into the coil sheath to close the clip leg portions and the living tissue is ligatured by maintaining the clip leg portions in the closed state.

DISCLOSURE OF INVENTION

In the ligation apparatus described in Jpn. Pat. Appln. KOKAI Publication No. 2004-121485, once the pressing pipe is fitted on the clip, the pair of arms can not be opened again, and living tissue can not be re-grasped. Therefore, in the ligation apparatus described in Jpn. Pat. Appln. KOKAI Publication No. 2004-121485, there is a possibility that living tissue cannot be ligatured properly.

Here, in the ligation apparatus, sharp claw portions are generally formed on the clip in order to grasp living tissue securely. In the ligation apparatus described in International Publication No. 03/030746A1 Pamphlet, the clip can not be accommodated in the coil sheath, so that the claw portions of the clip are exposed from the coil sheath. Therefore, when the ligation apparatus is inserted into a channel of an endoscope or the like, there is a possibility that a channel inner wall is damaged by the claw portion, or the claw portion is caught by the channel inner wall, which results in increase in required insertion force amount. Therefore, the ligation apparatus described in International Publication No. 03/030746A1 Pamphlet is improper for insertion into a body cavity.

The present invention has been made in view of the above problem, and an object thereof is to provide an optimal ligation apparatus for ligaturing living tissue in a body cavity.

According to an aspect of the present invention, a ligation apparatus is characterized by comprising: a clip including a clip claw member that is configured to open and close and ligatures a living tissue and a pressing member in which the clip claw member is accommodated and configured to advance and retreat, the clip claw member being advanced and retreated relative to the pressing member to be opened and closed according to interaction with the pressing member; a sheath which is configured to accommodate the clip such that the clip is configured to advance and retreat and such that the clip claw member is not exposed to the outside; an operation wire which is inserted through the sheath to be configured to advance and retreat, whose distal end portion is connected to the clip claw member, and which is configured to advance and retreat the clip relative to the sheath; an advance and retreat restricting mechanism which restricts advance and retreat of the pressing member relative to the sheath at a distal end portion of the sheath to allow advance and retreat of the clip claw member relative to the pressing member according to advance and retreat of the operation wire relative to the sheath so as to allow the clip ligaturing the living tissue; and a releasing mechanism which releases at least one portion of the clip from the sheath in a state that the clip ligatures the living tissue.

According to a preferred aspect of the present invention, the ligation apparatus is characterized in that the advance and retreat restricting mechanism includes a retreat restricting mechanism which restricts retreat of the pressing member relative to the sheath and an advance restricting mechanism which restricts advance of the pressing member relative to the sheath.

According to a preferred aspect of the present invention, the ligation apparatus is characterized in that the retreat restricting mechanism includes a retreat restriction abutting portion which is provided on the pressing member, and a retreat restricting stopper which is provided on the sheath and configured to abut the retreat restriction abutting portion disposed in front of the retreat restricting stopper to restrict retreat of the pressing member.

According to a preferred aspect of the present invention, the ligation apparatus is characterized in that the pressing member is configured to be projected from the distal end portion of the sheath and withdrawn therein, the retreat restriction abutting portion includes a blade portion which is provided on the pressing member, configured to be elastically expand and opened, and, shrink and closed, and which is shrunk and closed when the pressing member is accommodated in the sheath and is expanded and opened when the pressing member protrudes from the sheath; the retreat restricting stopper is provided at a distal end portion of the sheath and configured to abut the expanded and opened blade portion so that the pressing member is restricted to be entered into the distal end portion of the sheath.

According to a preferred aspect of the present invention, the ligation apparatus is characterized in that the pressing member and the sheath are approximately cylindrical, the retreat restriction abutting portion is formed of a retreat restricting large diameter portion whose outer diameter is increased in the pressing member, and the retreat restricting stopper is formed of a retreat restricting sheath small diameter portion whose inner diameter is decreased in the pressing member.

According to a preferred aspect of the present invention, the ligation apparatus is characterized in that the operation wire is advanced and retreated relative to the sheath, the clip is advanced and retreated relative to the sheath in a range where the retreat restricting large diameter portion does not abut the retreat restricting sheath small diameter portion, and the clip claw member is opened and closed by interaction with the sheath, so that temporary ligaturing of the living tissue is performed, and in a state that the retreat restricting large diameter portion abuts the retreat restricting sheath small diameter portion, the operation wire is retreated relative to the sheath and the clip claw member is retreated relative to the pressing member so that primary ligaturing of living tissue is performed.

According to a preferred aspect of the present invention, the ligation apparatus is characterized in that, when the living tissue is primarily ligatured, the clip claw member is fixed to the pressing member by frictional force.

According to a preferred aspect of the present invention, the ligation apparatus is characterized in that the advance restricting mechanism includes an advance restriction abutting portion which is provided on the pressing member, and an advance restricting stopper which is provided on the sheath and is configured to abut the advance restriction abutting portion disposed in rear of advance restricting stopper to restrict advance of the pressing member.

According to a preferred aspect of the present invention, the ligation apparatus is characterized in that the pressing member and the sheath are approximately cylindrical, the advance restriction abutting portion is formed of an advance restricting large diameter portion whose outer diameter is increased in the pressing member, and the advance restricting stopper is formed of an advance restricting sheath small diameter portion whose inner diameter is decreased in the sheath.

According to a preferred aspect of the present invention, the ligation apparatus is characterized in that the advance restricting mechanism includes an advance restriction abutting portion provided on the pressing member and an advance restricting stopper provided on the sheath and is configured to abut the advance restriction abutting portion to restrict advance of the pressing member, and when the pressing member is advanced relative to the sheath so that the advance restriction abutting portion abut the advance restricting stopper, the blade portion is expanded and opened.

According to a preferred aspect of the present invention, the ligation apparatus further comprises a connection member connecting a distal end portion of the operation wire and the clip claw member to each other, wherein the releasing mechanism includes a first breaking portion which is provided on the connection member and which is broken to separate the clip claw member from the distal end portion of the operation wire, and a second breaking portion which is provided on a distal end of the advance restriction abutting portion in the pressing member and which is broken to separate the distal end of the pressing member from the sheath.

According to a preferred aspect of the present invention, the ligation apparatus is characterized in that the second breaking portion includes a fragile portion whose strength is weaker than the other portion of the pressing member.

According to a preferred aspect of the present invention, the ligation apparatus is characterized in that, regarding a cross-section perpendicular to advancing and retreating directions of the pressing member, a sectional area of the fragile portion is smaller than that of the other portion of the pressing member.

According to a preferred aspect of the present invention, the ligation apparatus is characterized in that the releasing mechanism includes an engagement portion provided on a rear end of the first breaking portion on the connection member and an engagement reception portion provided on a rear end of the second breaking portion on the pressing member, and according to retreat of the operation wire relative to the sheath, the first breaking portion is broken, the connection member is retreated, the engagement portion is engaged with the engagement reception portion, the engagement reception portion is biased toward the rear end, and the second breaking portion is broken.

According to a preferred aspect of the present invention, the ligation apparatus is characterized in that the pressing member is approximately cylindrical and the connection member is approximately cylindrical, the engagement portion is formed of an engagement large diameter portion whose outer diameter is increased on the connection member, and the engagement reception portion is formed of an engagement small diameter portion whose inner diameter is decreased on the pressing member.

According to a preferred aspect of the present invention, the ligation apparatus further comprises a connection member connecting a distal end portion of the operation wire and the clip claw member to each other, wherein the advance restricting mechanism includes a biasing portion provided on the distal end portion of the operation wire, and a diameter-expanding and shrinking portion which is provided on the pressing member and configured to be elastically diameter-expand and shrink and which is biased and expanded in a diametrically outward direction of the pressing member by the biasing portion to form the advance restricting large diameter portion, and the releasing mechanism includes a first breaking portion provided on the connection member and configured to be broken to separate the clip claw member from the distal end portion of the operation wire, the biasing portion, and the diameter-expanding and shrinking portion, and according to retreat of the operation wire relative to the sheath, the first breaking portion is broken, the biasing portion is retreated toward the rear end beyond the diameter-expanding and shrinking portion so that the diameter-expanding and shrinking portion is diameter-shrunk, so that the pressing member is allowed to pass through the advance restricting sheath small diameter portion toward the distal end.

According to a preferred aspect of the present invention, the ligation apparatus is characterized in that the expanding and shrinking diameter portion includes a projecting portion which projects in a diametrical inward direction of the pressing member and is biased in a diametrically outward direction of the pressing member by the biasing portion.

According to a preferred aspect of the present invention, the ligation apparatus is characterized in that the pressing member includes an elastic portion which is configured to advance the clip claw member relative to the pressing member.

According to a preferred aspect of the present invention, the ligation apparatus is characterized in that the elastic portion is elastically deformed by retreating the operation wire relative to the sheath and retreating the clip claw member relative to the pressing member, and the elastic portion advances the clip claw member relative to the pressing member by a repulsive force produced when releasing the operation wire.

According to a preferred aspect of the present invention, the ligation apparatus is characterized in that the pressing member includes a bridge portion which forcibly opens the clip claw member when the clip claw member is advanced relative to the pressing member.

According to a preferred aspect of the present invention, the ligation apparatus is characterized in that the pressing member is approximately cylindrical and includes an opening and closing small diameter portion whose inner diameter is decreased, the clip claw member includes a pair of arm portions which is opened and closed to each other, the pair of the arm portions includes at least two crossing portions which are crossed to each other and top portions with a folded shape provided on the respective arm portions between the two crossing portions, and according to advance of the clip claw member relative to the pressing member, the top portions are inserted into the opening and closing small diameter portion to be approached to each other by the opening and closing small diameter portion so that the pair of arm portions is opened, and according to retreat of the clip claw member relative to the pressing member, the top portions are pulled out from the opening and closing small diameter portion to be spaced from each other so that the pair of arm portions is closed.

BRIEF DESCRIPTION OF DRAWINGS

FIG. 2 is a perspective view showing a clip of the ligation apparatus of the first embodiment of the present invention;

FIG. 3 is a perspective view showing a formation of bridge portions of a pressing member of the ligation apparatus of the first embodiment of the present invention;

BEST MODE FOR CARRYING OUT THE INVENTION

A first embodiment of the present invention will be explained with reference to FIGS. 1 to 8. In a ligation apparatus of this embodiment, a clip 26 is detachably attached to an apparatus main body 24.

Figure 1:
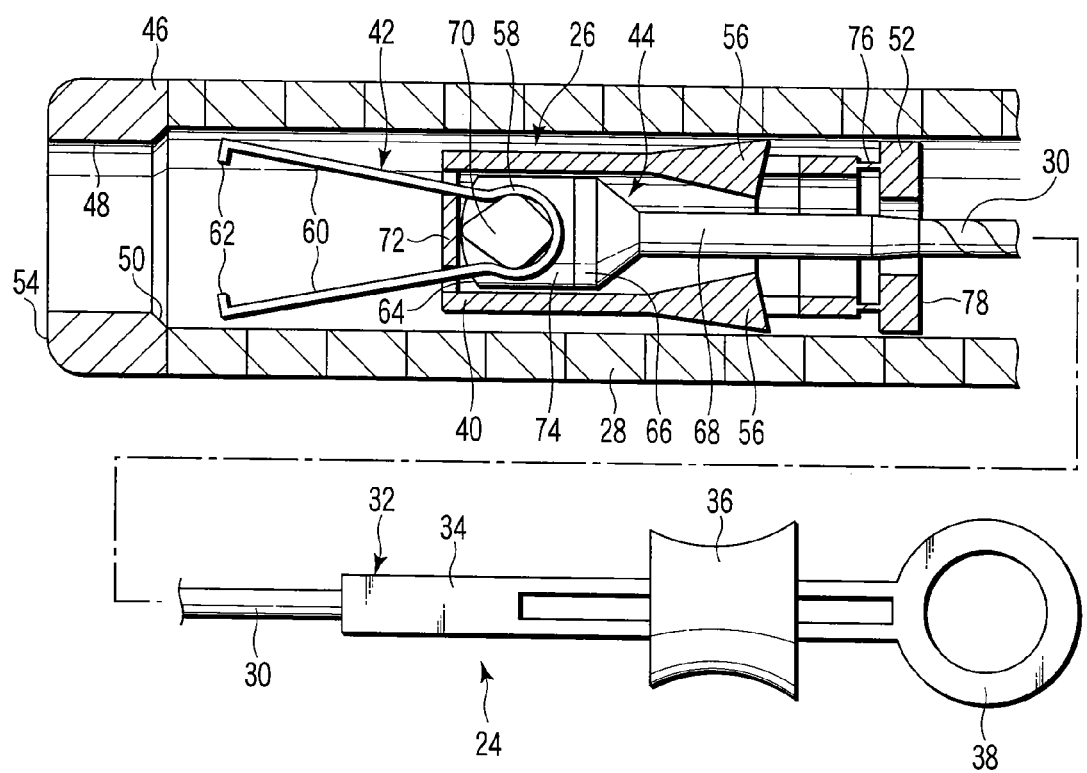
FIG. 1 is a view showing a ligation apparatus of a first embodiment of the present invention.

Referring to FIG. 1, the apparatus main body 24 includes a flexible sheath 28 that pass through a channel of an endoscope and is inserted into a body cavity. In the embodiment, the sheath 28 is formed by winding a coil tightly. An operation wire 30 for operating a clip 26 is inserted through the sheath 28 and configured to advance and retreat. A control portion 32 for operating the operation wire 30 to advance and retreat is coupled to a proximal end portion of the sheath 28. The control portion 32 includes an elongated control portion main body 34 extending in front and rear direction, and a slider 36 is disposed on the control portion main body 34 and configured to advance and retreat. A proximal end portion of the operation wire 30 is coupled to the slider 36, so that the operation wire 30 is advanced and retreated relative to the sheath 28 by advancing and retreating the slider 36 with respect to the control portion main body 34. A ring-like finger catching portion 38 is disposed on a rear end portion of the control portion main body 34 in order to hold the control portion main body 34 during advancing and retreating operation of the slider 36.

Referring to FIGS. 1 and 2, the clip 26 is accommodated at a distal end portion of the sheath 28 of the apparatus main body 24 and configured to advance and retreat. The clip 26 is formed by fitting a clip claw member 42 into an approximately cylindrical main body of the pressing member 40. The clip claw member 42 is connected with a distal end portion of the operation wire 30 via a connection member 44, and the clip claw member 42 and the pressing member 40 are advanced and retreated together relative to the sheath 28 by advancing and retreating the operation wire 30 relative to the sheath 28.

Advance and retreat restricting mechanisms that respectively restrict advance and retreat of the pressing member 40 relative to the sheath 28 at the distal end portion of the sheath 28 will be explained below.

The advance restricting mechanism that restricts advance of the pressing member 40 relative to the sheath 28 will be first explained in detail.

A circularly-annular stopper member 46 having an outer diameter approximately equal to an outer diameter of the coil and an inner diameter smaller than an inner diameter of the coil is fixed at a distal end portion of the coil by welding or the like. That is, a distal end of the sheath 28 is formed in a flange shape, and a sheath small diameter portion 48 whose inner diameter is decreased is formed at the distal end of the sheath 28. An advance restricting stopper 50 is formed at a rear end of the sheath small diameter portion 48. On the other hand, an advance restricting large diameter portion 52 whose outer diameter is increased is formed at a rear end portion of the pressing member 40. The advance restricting large diameter portion 52 configured to abut the advance restricting stopper 50 so that advance of the pressing member 40 relative to the sheath 28 is restricted.

Then, the retreat restricting mechanism that restricts retreat of the pressing member 40 relative to the sheath 28 will be explained in detail.

An outer diameter of a main body portion of the pressing member 40 is smaller than an inner diameter of the sheath small diameter portion 48, and the pressing member 40 is configured to protrude from the distal end portion of the sheath 28. A retreat restricting stopper 54 is formed of a distal end of the sheath small diameter portion 48. On the other hand, a plurality of blade portions 56 is arranged on the pressing member 40 and configured to elastically expand and open, and, shrink and close. That is, the blade portion 56 with elasticity is accommodated in a slit of the pressing member 40 extending in a longitudinal direction, and a distal end portion of the blade portion 56 is connected to the main body portion of the pressing member 40 at a distal end of the slit. A rear end portion of the blade portion 56 is configured to be elastically pivoted about a connection portion between the distal end portion of the blade portion 56 and the main body portion of the pressing member 40. The blade portion 56 is expanded and opened in a natural state where an external force is not applied to the blade portion 56.

When the pressing member 40 is accommodated in the sheath 28, the blade portions 56 are biased by an inner peripheral face of the sheath 28 to be folded into the slits. When the pressing member 40 protrude from the distal end portion of the sheath 28, the blade portions 56 are expanded and opened elastically. The expanded and opened blade portions 56 is configured to abut the retreat restricting stopper 54 so that retreat of the pressing member 40 relative to the sheath 28 is restricted.

Incidentally, a length of the sheath small diameter portion 52 along a central axis direction thereof is set to be slightly shorter than a length between a distal end face of the advance restricting large diameter portion 52 of the pressing member 40 and a rear end face of the expanded and opened blade portion 52. That is, in such a case that the clip 26 is advanced relative to the sheath 28, the blade portions 56 are expanded and opened just when the advance restricting large diameter portion 52 of the pressing member 40 abuts the advance restricting stopper 50.

An opening and closing mechanism of the clip claw member 42 will be explained below.

The clip claw member 42 is formed by bending a strip member made from stainless steel in a V shape such that a bent portion at a central portion of the strip member is formed in an arc shape and bending inwardly a pair of distal end portions of the V-shaped strip member so as to face each other. Here, an engagement portion 58 engaged with the connection member 44 is formed of an arc-shaped bent portion of the clip claw member 42. A pair of arm portions 60 that is opened and closed to each other to grasp living tissue is formed of a pair of arm-shaped portions protruding from the arc-shaped bent portion, and claw portions 62 punctured into living tissue are formed of hook-shaped portions at distal end portions of the pair of arm-shaped portion.

The connection member 44 connecting the distal end portion of the operation wire 30 and the clip claw member 42 includes a figure obtained by sequentially connecting a semi-cylindrical portion 64, a large cylindrical portion 66, and a small cylindrical portion 68 from a distal end of the connection member 44 in the order approximately coaxial, and it is accommodated in the pressing member 40. The semi-cylindrical portion 64 has a shape equal to that of one of two halves obtained by dividing a cylindrical shape having an outer diameter approximately equal to that of the large cylindrical portion 66 at a plane including the central axis. A teardrop-shaped engagement reception portion 70 is projected from a flat face portion of the semi-cylindrical portion 64, and the engagement portion 58 of the clip claw member 42 is winded on the engagement reception portion 70. A taper shape having an outer diameter that becomes smaller toward a rear end thereof is formed on a rear end of the large cylindrical portion 66, and the small cylindrical portion 68 having an outer diameter smaller than that of the large cylindrical portion 66 is connected to the taper-shaped rear end portion. The distal end portion of the operation wire 30 is connected to a proximal end portion of the small cylindrical portion 68 by bonding, welding, or the like. Here, when advance and retreat of the pressing member 40 relative to the sheath 28 is restricted, the connection member 44, namely, the clip claw member 42, is advanced and retreated relative to the pressing member 40 by advancing and retreating the operation wire 30 relative to the sheath 28.

Bridge portions 72 are bridged on the distal end portion of the pressing member 40 in a diametrical direction so as to cross a distal end opening of the distal end portion. The distal end opening is divided into two openings by these bridge portions 72, and the pair of arm portions 60 of the clip claw member 42 is slidably inserted into a pair of divided openings, respectively. The clip claw member 42 is advanced relative to the pressing member 40 so that the pair of arm portions 60 is biased and opened by the bridge portions 72, and the clip claw member 42 is opened. Incidentally, as shown in FIG. 3, the bridge portions 72 can be formed by bending elongated plate-shaped pieces projected in a direction of the central axis symmetrically about the central axis inwardly in the distal end face of the pressing member 40. On the other hand, the clip claw member 42 is retreated relative to the pressing member 40 so that the clip claw member 42 is withdrawn into the pressing member 40 and the clip claw member 42 is closed by the pressing member 40.

A releasing mechanism for releasing the clip 26 from the distal end portion of the sheath 28 will be explained below.

As described above, the clip claw member 42 and the distal end portion of the operation wire 30 are connected to each other by the connection member 44. A portion between the engagement reception portion 70 and the large cylindrical portion 66 at the semi-cylindrical portion 64 of the connection member 44 is made breakable, and it forms a first breaking portion 74. Incidentally, the first breaking portion 74 may be formed by reducing the diameter of the semi-cylindrical portion 64 to make strength thereof weak. When retreat of the pressing member 40 relative to the sheath 28 is restricted and the clip claw member 42 is withdrawn into the pressing member 40 sufficiently, the first breaking portion 74 is broken by further retreating the operation wire 30 relative to the sheath 28.

A second breakable breaking portion 76 is formed between the advance restricting large diameter portion 52 of the pressing member 40 and the blade portions 56. The second breaking portion 76 is formed of a fragile portion with weak strength, and a sectional area of the fragile portion is made smaller than that of the main body portion of the pressing member 40 regarding a cross-section perpendicular to the central axis direction of the pressing member 40. In the embodiment, the fragile portion is formed by thinning the thickness of the pressing member 40, but it may be formed by forming a slit or the like. An engagement small diameter portion 78 whose inner diameter is reduced relative to the main body portion of the pressing member 40 is formed at a rear end of the second breaking portion 76. When the first breaking portion 74 is broken, the tapered shape at the rear end of the large cylindrical portion 66 serving as an engagement large diameter portion is engaged with the engagement small diameter portion 78 of the pressing member 40 according to retreat of the operation wire 30 relative to the sheath 28, thereby biasing the engagement small diameter portion 78 toward the rear end to break the second breaking portion 76.

Next, referring to FIGS. 4 to 8, the ligaturing method of living tissue using the ligation apparatus of the embodiment will be explained. In the embodiment, the ligation apparatus is used in combination with an endoscope.

Figure 4:
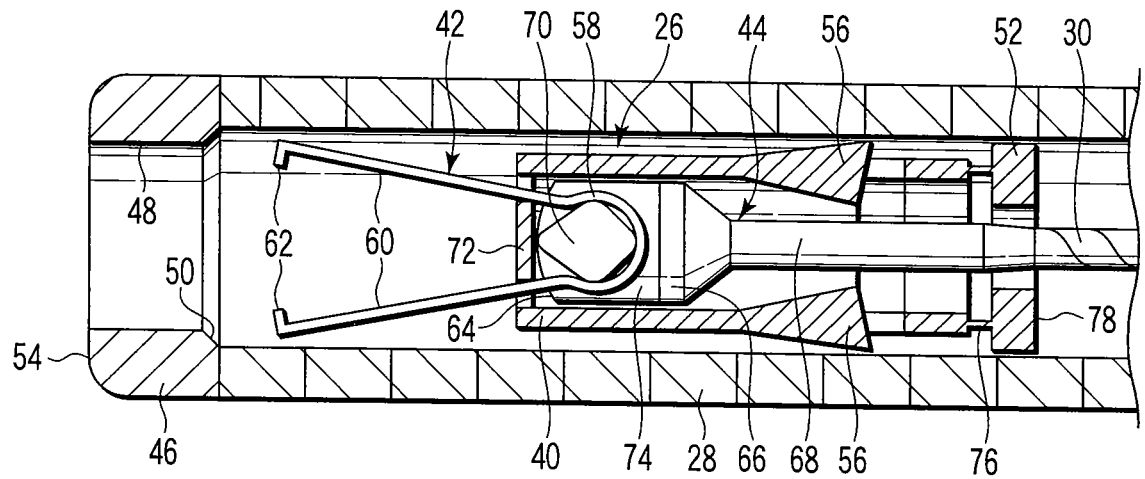
FIG. 4 is a longitudinal sectional view for explaining a step of accommodating a clip into a sheath in a ligaturing method using the ligation apparatus of the first embodiment of the present invention.

Referring to FIG. 4, attachment is performed such that the clip 26 is completely accommodated in the distal end portion of the sheath 28. In the attached state, the clip claw member 42 is not exposed to the outside and the blade portions 56 of the pressing member 40 are elastically shrunk and closed by an inner peripheral face of the sheath 28 to be folded into the slits. Incidentally, the clip claw member 42 is disposed at the front end position relative to the pressing member 40 and the clip claw member 42 is biased to be opened to a maximum extent by the bride portions 72, but it is elastically closed by the inner peripheral face of the sheath 28.

Then, the sheath 28 is inserted through a channel of the endoscope inserted into a body cavity and the distal end portion of the sheath 28 is inserted into the body cavity by protruding the distal end portion of the sheath 28 from the distal end portion of the channel. The distal end portion of the sheath 28 is moved near a section to be ligatured A of living tissue under observation performed by the endoscope. Incidentally, the sheath 28 may be inserted into a body cavity using a channel of a guiding equipment other than the endoscope.

Figure 5:
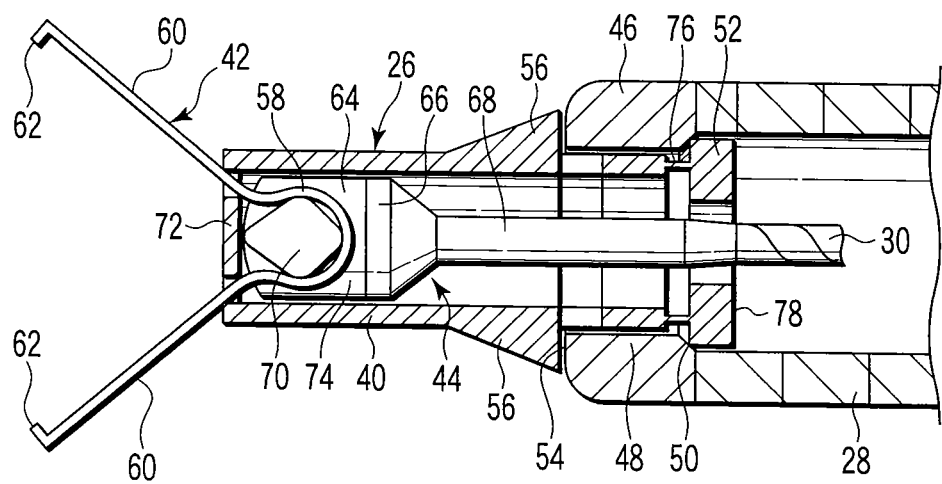
FIG. 5 is a longitudinal sectional view for explaining a step of restricting advance and retreat of the pressing member in the ligaturing method using the ligation apparatus of the first embodiment of the present invention.

Referring to FIG. 5, the slider 36 is advanced relative to the control portion main body 34 in the control portion 32 and the clip 26 is advanced relative to the sheath 28 by the operation wire 30 so that the clip 26 protrude from the distal end portion of the sheath 28. At the time, the advance restricting large diameter portion 52 of the pressing member 40 abuts the advance restricting stopper 50 of the sheath small diameter portion 48 so that the pressing member 40 is prevented from being further protruded from the distal end portion of the sheath 28. Simultaneously, the pressing member 40 protrudes from the distal end portion of the sheath 28 so that restriction performed by the inner peripheral face of the sheath 28 is released and the blade portions 56 of the pressing member 40 are expanded and opened, and the expanded and opened blade portions 56 abuts the retreat restricting stopper 54 at the distal end of the sheath 28 so that the pressing member 40 is restricted entering into the distal end portion of the sheath 28. Biasing to the clip claw member 42 by the inner peripheral face of the sheath 28 is released so that the clip claw member 42 is opened to a maximum extent.

Figure 6:
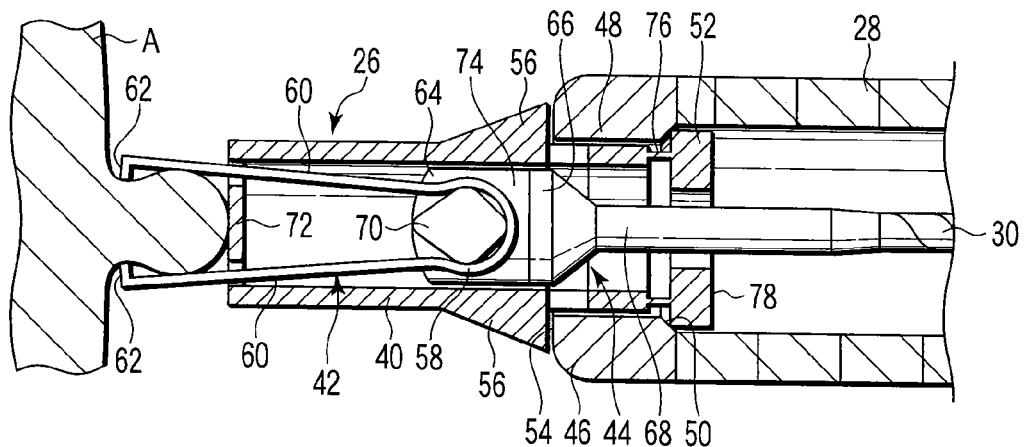
FIG. 6 is a longitudinal sectional view for explaining a step of grasping living tissue in the ligaturing method using the ligation apparatus of the first embodiment of the present invention.

Referring to FIG. 6, the sheath 28 of the ligation apparatus is pushed relative to the endoscope and the distal end portion of the clip claw member 42 is pressed onto the portion to be ligatured A of the living tissue under observation performed by the endoscope. The slider 36 is retreated relative to the control portion main body 34 of the ligation apparatus. As a result, the clip claw member 42 is retreated relative to the pressing member 40 by the operation wire 30, and the clip claw member 42 is withdrawn into the pressing member 40, so that the clip claw member 42 is closed by the pressing member 40. The claw portions 62 of the clip claw member 42 are punctured into the portion to be ligatured A and living tissue is grasped by the clip claw member 42. The clip claw member 42 is sufficiently closed by sufficiently withdrawing the clip claw member 42 into the pressing member 40, so that the living tissue is ligatured.

Here, when the portion to be ligatured A is properly ligatured in ligature for hemostasis, bleed is stopped, but when proper ligature can not be achieved, hemostasis can not be obtained so that re-ligature is necessary. When re-ligature is performed, the slider 36 is advanced relative to the control portion main body 34 of the ligation apparatus. As a result, the clip claw member 42 is advanced relative to the pressing member 40 by the operation wire 30, so that the clip claw member 42 is biased and opened by the bridge portions 72. Thus, the portion to be ligatured A is released. Thereafter, the above-described operation is repeated until the portion to be ligatured A is properly ligatured.

Figure 7:
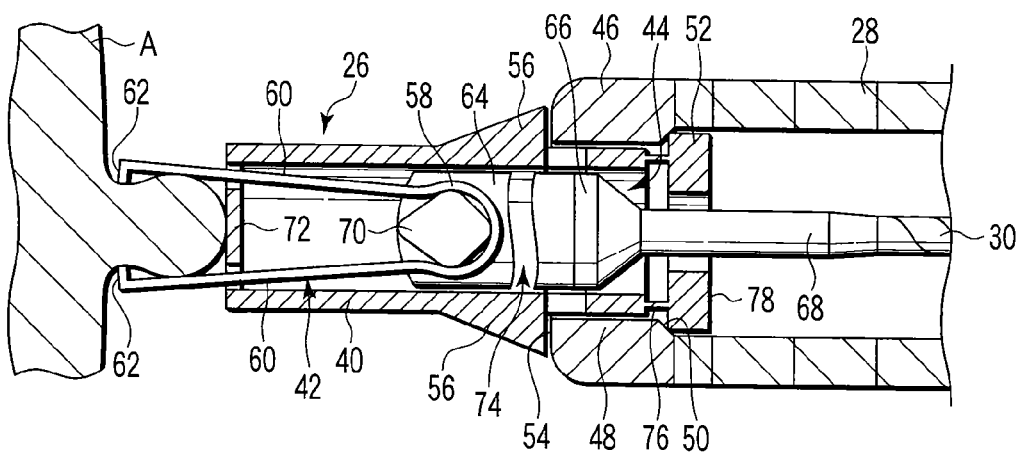
FIG. 7 is a longitudinal sectional view for explaining a step of separating a clip claw portion in the ligaturing method using the ligation apparatus of the first embodiment of the present invention.

Referring to FIG. 7, the slider 36 is further retreated relative to the control portion main body 34 in a state that the portion to be ligatured A has been properly ligatured and the clip claw member 42 has been sufficiently withdrawn into the pressing member 40. As a result, the first breaking portion 74 of the connection member 44 is broken and the clip claw member 42 is separated from the operation wire 30.

Figure 8:
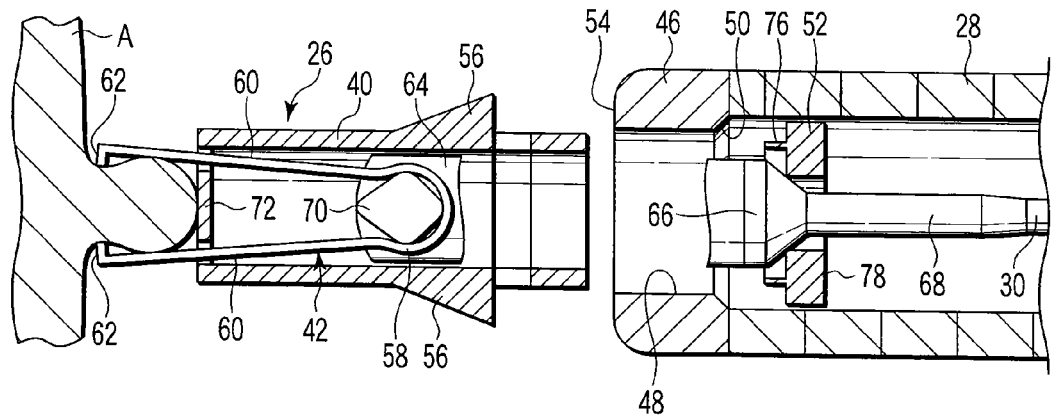
FIG. 8 is a longitudinal sectional view for explaining a step of releasing the clip in the ligaturing method using the ligation apparatus of the first embodiment of the present invention.

Referring to FIG. 8, after the first breaking portion 74 has been broken, the slider 36 is further retreated relative to the control portion main body 34. As a result, the large cylindrical portion 66 of the connection member 44 is engaged with the engagement small diameter portion 78 of the pressing member 40 and the engagement small diameter portion 78 is biased toward the rear end by the large cylindrical portion 66, so that the fragile portion of the pressing member 40 is broken. Thus, the distal end portion of the pressing member 40 is separated from the distal end portion of the sheath 28.

Thereafter, the sheath 28 is pulled out relative to the endoscope and the clip 26 is released from the distal end portion of the sheath 28. Here, the clip claw member 42 is engaged with the pressing member 40 through frictional resistance therebetween and it is maintained in a closed state. Therefore, the clip 26 is left in the body cavity while ligaturing the portion to be ligatured A.

Accordingly, the ligation apparatus of the embodiment achieves the following effect. In the ligation apparatus of the embodiment, the clip 26 is accommodated in the sheath 28 such that the clip claw member 42 is not exposed to the outside and it is inserted into a body cavity by inserting the sheath 28 into the channel of the endoscope or the like. Therefore, a channel inner wall is prevented from being injured by the clip claw member 42 and increase of a required amount of insertion force due to that the clip claw member 42 is caught by the channel inner wall is avoided. The clip claw member 42 is advanced and retreated relative to the pressing member 40 to be opened and closed according to interaction with the pressing member 40, and the advance and retreat restricting mechanism restricts advance and retreat of the pressing member 40 relative to the sheath 28 at the distal end portion of the sheath 28 and so enables advance and retreat of the clip claw member 42 relative to the pressing member 40 according to advance and retreat of the operation wire 30 relative to the sheath 28 such that living tissue can be ligatured by the clip 26. Therefore, the portion to be ligatured A can be re-ligatured by the clip claw member 42. Thus, the ligation apparatus of the embodiment is an optimal apparatus for ligaturing living tissue in a body cavity.

In the ligation apparatus of the embodiment, according to advance of the slider 36 relative to the control portion main body 34, the clip 26 protrudes from the distal end portion of the sheath 28 and the clip claw member 42 is opened, and, subsequently, according to retreat of the slider 36 relative to the control portion main body 34, the clip claw member 42 is closed and the clip 26 is released from the distal end portion of the sheath 28. Thus, an operation direction in the proximal end portion of the ligation apparatus and an actuation direction at the distal end portion of the ligation apparatus coincide with each other so that an intuitive operation performed to the ligation apparatus is made possible.

Further, in the clip 26 of the ligation apparatus of the embodiment, when the clip claw member 42 is advanced relative to the pressing member 40, the clip claw member 42 is forcibly opened by the bridge portions 72. If such bridge portions 72 are not formed, the clip claw member 42 is opened by only expansion biasing to the clip claw member 42, which results in difficulty in reliable opening of the clip claw member 42, but the clip claw member 42 can be reliably opened in the embodiment.

FIGS. 9 to 13 show a second embodiment of the present invention. Constitutions having functions similar to those of the first embodiment are attached with same reference numerals and explanation thereof is omitted.

The advance restricting mechanism for restricting advance of the pressing member 40 and the releasing mechanism for releasing the clip 26 will be explained below.

A diameter-expanding and shrinking portion 80 which can be elastically expand and shrink in diameter is formed at a rear end portion of the pressing member 40. The diameter-expanding and shrinking portion 80 in a diameter-expanded state has an outer diameter larger than an inner diameter of the sheath small diameter portion 48 and it has a function similar to that of the above advance restricting portion 52 (FIGS. 1 to 8). On the other hand, the diameter-expanding and shrinking portion 80 in a diameter-shrunk state has an outer diameter approximately equal to that of an approximately cylindrical main body portion of the pressing member 40 and smaller than an inner diameter of the sheath small diameter portion 48, so that the diameter-expanding and shrinking portion 80 can pass through the sheath small diameter portion 48.

The diameter-expanding and shrinking portion 80 has projecting portions 84 projecting inwardly in a diametrical direction of the pressing member 40. An approximately cylindrical biasing portion 86 having a diameter larger than an outer diameter of the operation wire 30 is integrally or separately formed at the distal end portion of the operation wire 30. Incidentally, the small cylindrical portion 68 (FIGS. 1 and 8) is not formed on the connection member 40, which is different from the first embodiment, and the distal end portion of the biasing portion 86 is connected to a rear end portion of the large cylindrical portion 66 by bonding, mechanical connection, welding, or the like. The biasing portion 86 is inserted into the pressing member 40 to bias the projecting portions 84 in a diametrically outward direction of the pressing member 40 and to maintain the diameter-expanding and shrinking portion 80 in an expanded state. Here, a length of the biasing portion 86 along the central axis direction is set such that it is always put inside the projecting portions 84 in a diametrical direction to maintain the diameter-expanding and shrinking portion 80 in the diameter-expanded state when the clip claw member 42 is opened and closed according to advance and retreat of the clip claw member 42 relative to the pressing member 40. After the first breaking portion 74 of the connection member 44 is broken, when the biasing portion 86 is pulled out from the pressing member 40 by retreating the operation wire 30 relative to the sheath 28, biasing to the projecting portions 84 by the biasing portion 86 is released, the diameter-expanding and shrinking portion 80 is maintained in the diameter-shrunk state.

The opening and closing mechanism of the clip claw member 42 will be explained below. The clip claw member 42 of the embodiment includes two crossing portions 88 where a pair of arm portions 60 crosses each other. Respective arm portions 60 are bent such that top portions 90 are formed between these two crossing portions 88. On the other hand, a distal end portion of the pressing member 40 is formed in a flange shape and an opening and closing small diameter portion 92 having an inner diameter smaller than an inner diameter of the main body portion of the pressing member 40 is formed at the distal end portion of the pressing member 40. In the embodiment, front and rear end portions of the opening and closing small diameter portion 92 are each formed in a stepped shape, but they may be formed in another shape such as a slope shape. Here, a distance between the respective top portions 90 in a width direction of the clip 26 is larger than an inner diameter of the opening and closing small diameter portion 92 of the pressing member 40 in a natural state where an external force is not applied to the top portions 90 but it may be larger or smaller than the inner diameter of the main body portion of the pressing member 40. The respective top portions 90 are inserted into the opening and closing small diameter portion 92 by advancing the clip claw member 42 relative to the pressing member 40, so that they are approached each other in a diametrically inward direction of the pressing member 40 and the distal ends of the pair of arm portions 60 are opened. On the other hand, the respective top portions 90 are pulled out from the opening and closing small diameter portion 92 according to retreat of the clip claw member 42 relative to the pressing member 40, so that they are separated from each other in a diametrically outward direction of the pressing member 40 and the distal ends of the pair of arm portions 60 are closed.

Next, referring to FIGS. 9 to 13, a ligaturing method of living tissue using the ligation apparatus of the embodiment will be explained. Hereinafter, detailed explanation of steps similar to those in the first embodiment is omitted.

Figure 9:
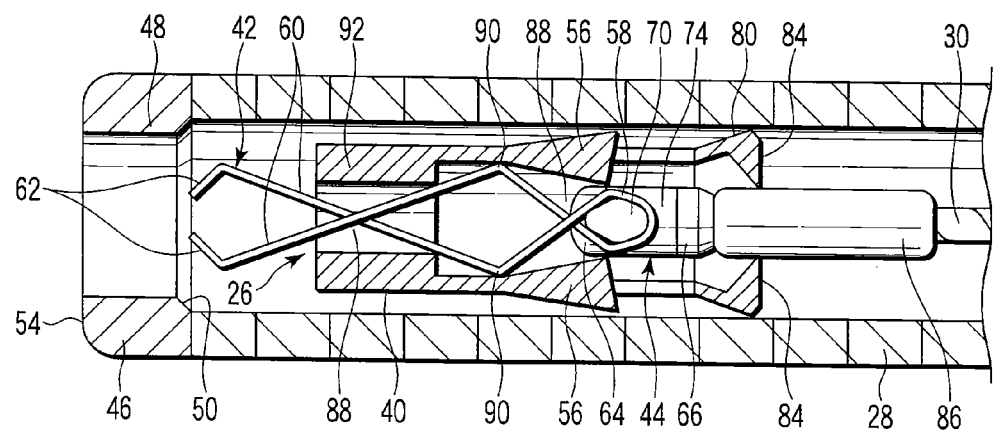
FIG. 9 is a longitudinal sectional view showing a distal end portion of a ligation apparatus of a second embodiment of the present invention, for explaining a step of accommodating a clip into a sheath in a ligaturing method using this ligation apparatus.

Referring to FIG. 9, the clip 26 is disposed near a portion to be ligatured A by accommodating the clip 26 at the distal end portion of the sheath 28 and inserting the distal end portion of the sheath 28 into a body cavity.

Figure 10:
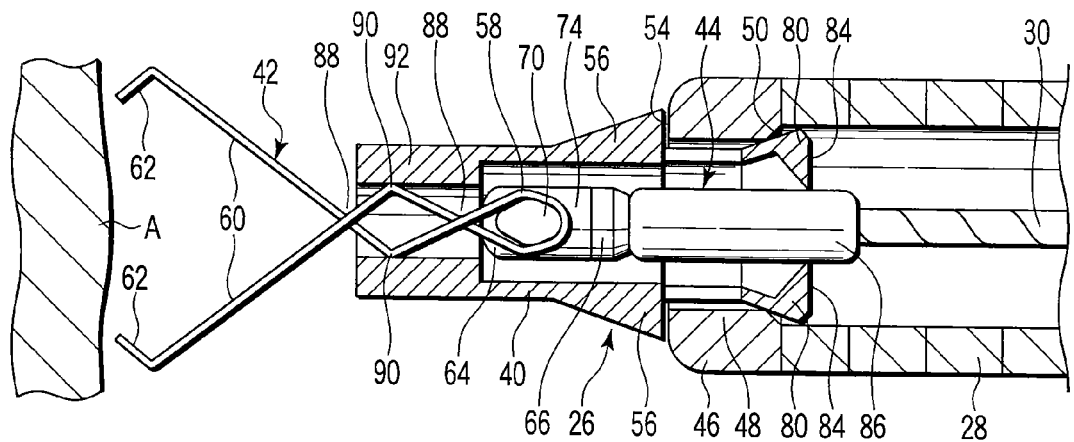
FIG. 10 is a longitudinal sectional view for explaining a step of restricting advance and retreat of a pressing member in the ligaturing method using the ligation apparatus of the second embodiment of the present invention.

Referring to FIG. 10, the projecting portions 84 are biased in a diametrically outward direction of the pressing member 40 by the biasing portion 86 at the distal end portion of the operation wire 30, and the diameter-expanding and shrinking portion 80 is maintained in a diameter-expanded state. In the state, the clip 26 is protruded from the distal end portion of the sheath 28 so that advance and retreat of the pressing member 40 relative to the distal end portion of the sheath 28 is restricted by the advance and retreat restricting mechanism. The slider 36 is advanced relative to the control portion main body 34 so that the clip claw member 42 is advanced relative to the pressing member 40 by the operation wire 30. As a result, the top portions 90 of the respective arm portions 60 of the clip claw member 42 are inserted into the opening and closing small diameter portion 92, so that the top portions 90 are approached to each other in the diametrically inward direction of the pressing member 40 and the distal ends of the pair of arm portions 60 are opened.

Figure 11:
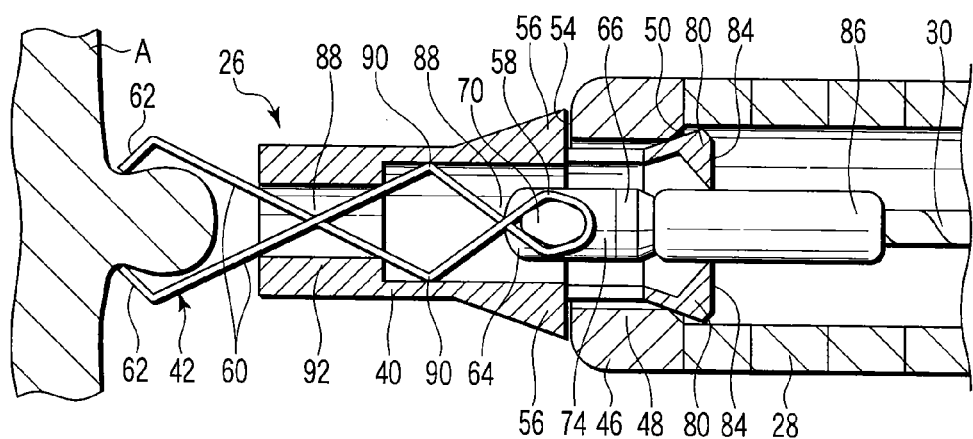
FIG. 11 is a longitudinal sectional view for explaining a step of grasping living tissue in the ligaturing method using the ligation apparatus of the second embodiment of the present invention.

Referring to FIG. 11, the distal end portions of the clip claw member 42 are pressed to a portion to be ligatured A of living tissue. The slider 36 is retreated relative to the control portion main body 34 of the ligation apparatus, so that the clip claw member 42 is retreated relative to the pressing member 40 by the operation wire 30. As a result, the top portions 90 of the respective arm portions 60 of the clip claw member 42 are pulled out of the opening and closing small diameter portion 92, so that the top portions 90 are separated from each other in the diametrically outward direction of the pressing member 40 and the distal ends of the pair of arm portions 60 are closed. Thus, the living tissue is ligatured. When the portion to be ligatured A can not be properly ligatured, the above-described opening and closing operation is repeated until the portion to be ligatured A is properly ligatured.

Figure 12:
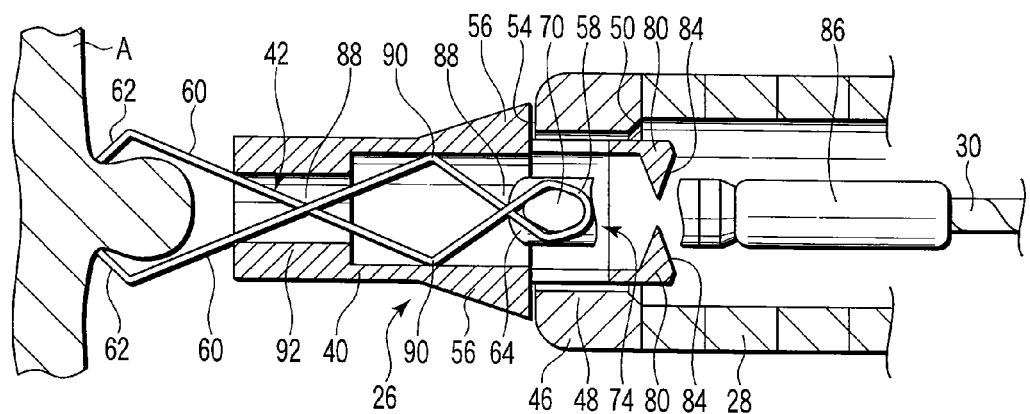
FIG. 12 is a longitudinal sectional view for explaining a step of separating a clip claw member and the pressing member from each other in the ligaturing method using the ligation apparatus of the second embodiment of the present invention.

Referring to FIG. 12, in a state that the portion to be ligatured A has been properly ligatured and the clip claw member 42 has been sufficiently withdrawn into the pressing member 40, the slider 36 is retreated relative to the control portion main body 34, the first breaking portion 74 of the connection member 44 is broken, and the clip claw member 42 is separated from the operation wire 30. After the first breaking portion 74 is broken, the slider 36 is further retreated relative to the control portion main body 34. As a result, the biasing portion 86 at the distal end portion of the operation wire 30 is pulled out from the pressing member 40, so that biasing to the projecting portions 84 by the biasing portion 86 is released and the diameter-expanding and shrinking portions 80 are elastically transferred to a diameter-shrunk state, where the diameter-expanding and shrinking portion 80 can pass through the sheath small diameter portion 48. Thus, the pressing member 40 is separated from the distal end portion of the sheath 28.

Figure 13:
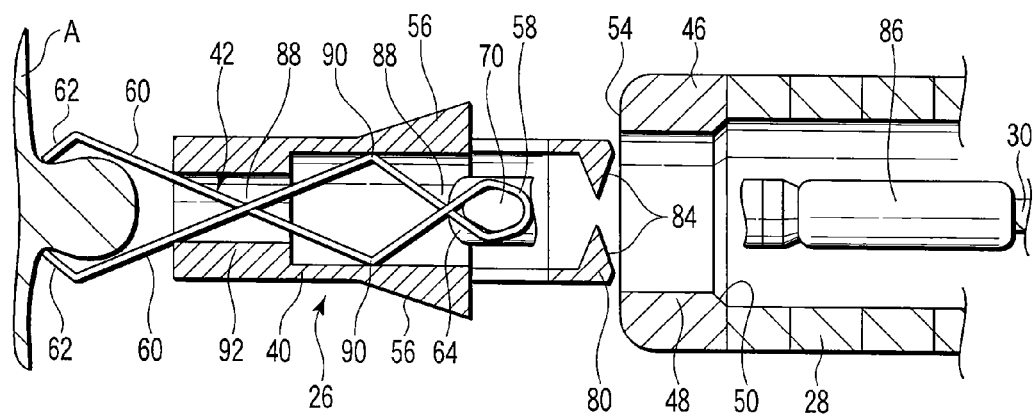
FIG. 13 is a longitudinal sectional view for explaining a step of releasing a clip in the ligaturing method using the ligation apparatus of the second embodiment of the present invention.

Referring to FIG. 13, the sheath 28 is pulled out from the endoscope and the clip 26 is released from the distal end portion of the sheath 28.

Accordingly, the ligation apparatus of the embodiment achieves the following effect. In the opening and closing mechanism of the clip claw member 42 of the embodiment, according to advance of the clip claw member 42 relative to the pressing member 40, the top portions 90 of the respective arm portions 60 of the clip claw member 42 are inserted into the opening and closing small diameter portion of the pressing member 40 and they are approached to each other by the opening and closing small diameter portion 92, so that the pair of arm portions 60 is opened. On the other hand, according to retreat of the clip claw member 42 relative to the pressing member 40, the top portions 90 are pulled out from the opening and closing small diameter portion 92 and they are separated from each other, so that the pair of arm portions 60 is closed. Therefore, even if opening and closing of the clip claw member 42 are repeated, reduction of an opening width due to plastic deformation of the clip claw member 42 can be prevented, and opening and closing of the clip claw member 42 can be repeated permanently despite of the material of the clip claw member 42.

In the releasing mechanism of the clip 26 of the embodiment, according to retreat of the slider 36 relative to the control portion main body 34, the biasing portion 86 is pulled out of the pressing member 40 by the operation wire 30, biasing to the projecting portions 84 imparted by the biasing portion 86 is released, and the diameter-expanding and shrinking portion 80 is elastically transferred to a diameter-shrunk state, where the diameter-expanding and shrinking portion 80 can pass through the sheath small diameter portion 48. Thus, separation between the pressing member 40 and the distal end portion of the sheath 28 is performed utilizing elastic deformation, where the separation can be reliably performed and a required amount of operation force is reduced as compared with the case that the separation is performed utilizing plastic deformation.

Figure 14:
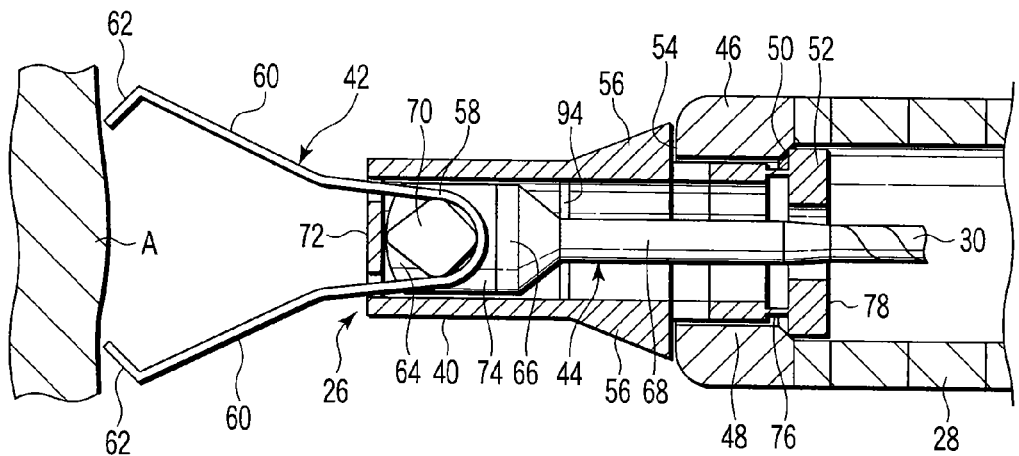
FIG. 14 is a longitudinal sectional view showing a distal end portion of a ligation apparatus of a third embodiment of the present invention.
Figure 15:
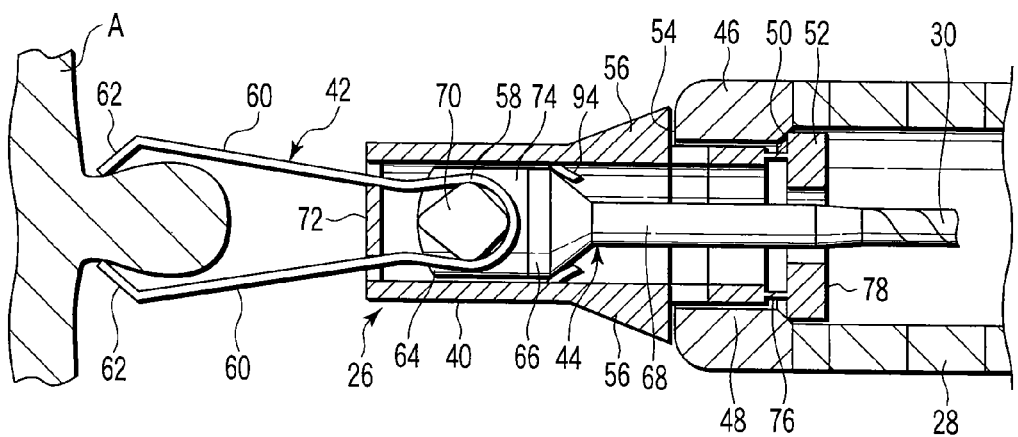
FIG. 15 is a longitudinal sectional view for explaining a step of grasping living tissue in a ligaturing method using the ligation apparatus of the third embodiment of the present invention.

FIGS. 14 and 15 show a third embodiment of the present invention. Constitutions having functions similar to those of the first embodiment are attached with same reference numerals and explanation thereof is omitted.

Referring to FIG. 14, the pressing member 40 of the embodiment includes an elastic portion for advancing the clip claw member 42 relative to the pressing member 40. The elastic portion is formed of a flat spring 94 projected from an inner peripheral face of the pressing member 40. The flat spring 94 may be formed integrally with the pressing member 40 or it may be connected to the pressing member 40 provided as a separating part by bonding, mechanical connection, welding, or the like. Like the first embodiment, the clip claw member 42 is disposed at a front end position relative to the pressing member 40 and the flat spring 94 is disposed at a position of a rear end portion of the large cylindrical portion 66 of the connection member 44. When the connection member 44 is retreated relative to the pressing member 40 according to retreat of the operation wire 30 relative to the sheath 28, the flat spring 94 is elastically deformed by the tapered shape of the large cylindrical portion 66 of the connection member 44, so that a repulsive force for advancing the connection member 44 is produced.

Next, referring to FIGS. 14 and 15, a ligaturing method of living tissue using the ligation apparatus of the embodiment will be explained. Detailed explanation of steps similar to those in the first embodiment is omitted below.

The slider 36 is retreated relative to the control portion main body 34 of the ligation apparatus so that the clip claw member 42 is closed to grasp living tissue. At the time, the connection member 44 is retreated relative to the pressing member 40, and the flat spring 94 is elastically deformed by a tapered shape of the large cylindrical portion 66 of the connection member 44, so that a repulsive force for advancing the connection member 44 is produced. When the portion to be ligatured A is not ligatured properly, operation force to the slider 36 is released. As a result, the clip claw member 42, the connection member 44, and the operation wire 30 are automatically advanced relative to the pressing member 40 or the sheath 28 by repulsive force of the flat spring 94, and the clip claw member 42 is opened so that the portion to be ligatured A is released. Thereafter, the above-described operation is repeated until the portion to be ligatured A is properly ligatured.

Accordingly, the ligation apparatus of the embodiment achieves the following effect. In such a configuration that an advance operation of the slider 36 relative to the operation main body portion is transmitted to the connection member 44 via the operation wire 30, such a case occurs that operation force is not sufficiently transmitted to the connection member 44 due to slack of the operation wire 30 so that the connection member 44 is not advanced securely. In the ligation apparatus of the embodiment, the clip claw member 42, the connection member 44, and the operation wire 30 are advanced relative to the pressing member 40 or the sheath 28 by elastic force of the flat spring 94 of the pressing member 40. Therefore, the connection member 44 can be advanced reliably and the clip claw member 42 can be opened and closed reliably.

According to only releasing operation force relative to the slider 36, the connection member 44 is automatically advanced relative to the pressing member 40 by elastic force of the flat spring 94. Therefore, operation for advance of the slider 36 relative to the control portion main body 34 is made unnecessary so that operation of the ligation apparatus is considerably simple.

Incidentally, the elastic portion of the embodiment can be also applied to the second embodiment.

Figure 16:
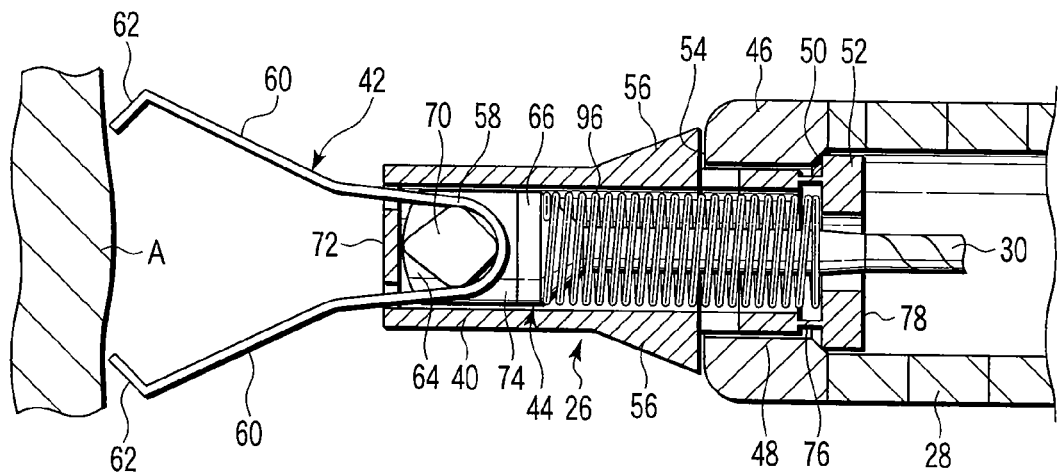
FIG. 16 is a longitudinal sectional view showing a distal end portion of a ligation apparatus of a fourth embodiment of the present invention.
Figure 17:
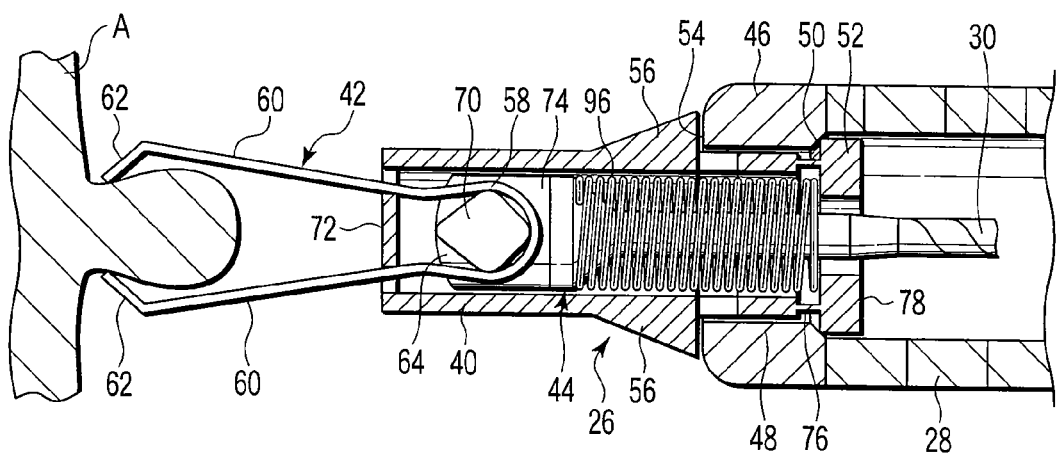
FIG. 17 is a longitudinal sectional view for explaining a step of grasping living tissue in a ligaturing method using the ligation apparatus of the fourth embodiment of the present invention.

FIGS. 16 and 17 show a fourth embodiment. Constitutions having functions similar to those of the third embodiment are attached with same reference numerals and explanation thereof is omitted.

The elastic portion of the embodiment is formed of a coil spring 96. The coil spring 96 is attached in the pressing member 40 and attached on the connection member 44 between the distal end portion of the tapered shape of the large cylindrical portion 66 of the connection member 44 and a distal end face of the engagement small diameter portion 78 of the pressing member 40. When operation force to the slider 36 is released, the clip claw member 42 is disposed at a front end position relative to the pressing member 40 and the coil spring 96 is not compressed. By retreating the operation wire 30 relative to the sheath 28 to retreat the connection member 44 relative to the pressing member 40, the coil spring 96 is compressed by the distal end portion of the tapered shape and the distal end face of the engagement small diameter portion 78, so that a repulsive force for advancing the connection member 44 is produced. The ligaturing method of living tissue by the ligation apparatus of the embodiment is similar to that of living tissue by the ligation apparatus of the third embodiment.

In the embodiment, since the coil spring 96 is used as the elastic portion, larger elastic force can be obtained reliably as compared with the case that the flat spring 94 is used like the third embodiment. Therefore, large force can be applied to the distal end of the connection member 44 so that the clip claw member 42 can be opened reliably.

FIGS. 18 to 22 show a fifth embodiment. Constitutions having functions similar to those of the first embodiment are attached with same reference numerals and explanation thereof is omitted.

The advance and retreat restricting mechanism for restricting advance and retreat of a pressing member 40 will be explained below.

The sheath small diameter portion 48 of the embodiment is disposed apart from the distal end of the sheath 28 by a distance. The sheath small diameter portion 48 is formed by crushing the sheath 28 from an outer peripheral face thereof to protrude the same in a diametrically inward direction or by connecting another member on an inner peripheral face of the sheath 28. The sheath small diameter portion 48 of the embodiment functions as an advance restricting sheath small diameter portion and a retreat restricting sheath small diameter portion. That is, the advance restricting stopper 50 for restricting advance of the pressing member 40 is formed of a rear end of the sheath small diameter portion 48. On the other hand, the retreat restricting stopper 54 for restricting retreat of the pressing member 40 is formed of a distal end of the sheath small diameter portion 48. The distal end portion of the pressing member 40 is formed in a flange shape, and a retreat restricting large diameter portion 98 whose outer diameter is increased is formed at the distal end portion of the pressing member 40. The retreat restricting large diameter portion 98 of the pressing member 40 is configured to abut the retreat restricting stopper 54 of the sheath small diameter portion 48, so that retreat of the pressing member 40 relative to the sheath 28 is restricted.

Here, when the retreat restricting large diameter portion 98 of the pressing member 40 abuts the advance restricting stopper 54 of the sheath small diameter portion 48, the pressing member 40 is positioned at a front end position with respect to the sheath 28, and the position of the pressing member 40 is called distal end restricting position. Incidentally, a length between the distal end of the sheath 28 and the advance restricting stopper 50 of the sheath small diameter portion 48 is set to be almost equal to or slightly shorter than a length between the distal end portion of the pressing member 40 and the distal end face of the advance restricting large diameter portion 52. That is, when the pressing member 40 is disposed at the distal end restricting position, the distal end portion of the pressing member 40 is disposed at a position of the distal end of the sheath 28 or slightly protruded from the distal end of the sheath 28. On the other hand, when the retreat restricting large diameter portion 98 of the pressing member 40 abuts the retreat restricting stopper 54 of the sheath small diameter portion 48, the pressing member 40 is positioned at a rear end position relative to the sheath 28 and the position of the pressing member 40 is called rear end restricting position.

When the pressing member 40 is disposed at the distal end restricting position, the operation wire 30 is advanced relative to the sheath 28 so that the clip claw member 42 is advanced relative to the pressing member 40, while the operation wire 30 is retreated relative to the sheath 28 so that the pressing member 40 and the clip claw member 42 are retreated together relative to the sheath 28. On the other hand, when the pressing member 40 is disposed at the rear end restricting position, the operation wire 30 is retreated relative to the sheath 28 so that the clip claw member 42 is retreated relative to the pressing member 40, while the operation wire 30 is advanced relative to the sheath 28 so that the pressing member 40 and the clip claw member 42 are advanced together relative to the sheath 28. When the pressing member 40 is disposed between the distal end restricting position and the rear end restricting position, the pressing member 40 and the clip claw member 42 are advanced and retreated together relative to the sheath 28 by advancing and retreating the operation wire 30 relative to the sheath 28, so that the clip claw member 42 is biased by the inner peripheral face of the sheath 28 to be opened and closed.

Next, referring to FIGS. 18 to 22, a ligaturing method using the ligation apparatus of the embodiment will be explained. The detailed explanation about steps similar to the first embodiment is omitted.

Figure 18:
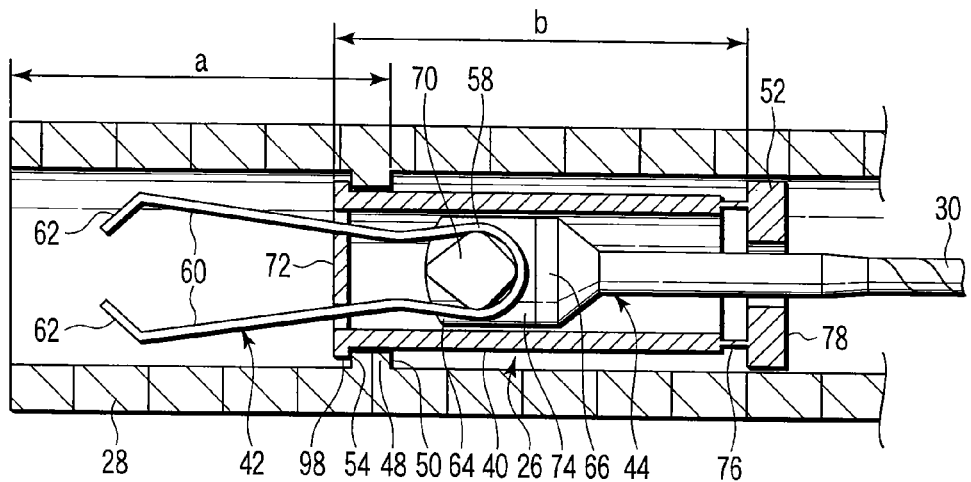
FIG. 18 is a longitudinal sectional view showing a distal end portion of a ligation apparatus of a fifth embodiment of the present invention, for explaining a step of restricting retreat of a pressing member in a ligaturing method using this ligation apparatus.

Referring to FIG. 18, a clip 26 is attached to a distal end portion of the sheath 28 and the slider 36 is retreated relative to the control portion main body 34. As a result, the clip 26 is retreated relative to the sheath 28, the pressing member 40 is disposed at the rear end restricting position, the clip claw member 42 is further retreated relative to the pressing member 40, and the clip claw member 42 is accommodated in the sheath 28 so as not be exposed to the outside. In the state, the distal end portion of the sheath 28 is inserted into a body cavity and it is disposed near a portion to be ligatured A of living tissue.

Figure 19:
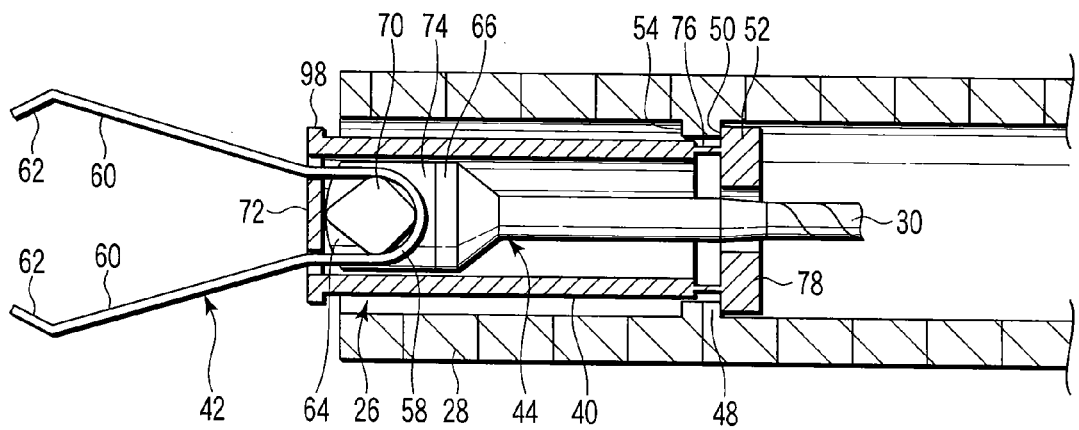
FIG. 19 is a longitudinal sectional view for explaining a step of restricting advance of the pressing member in the ligaturing method using the ligation apparatus of the fifth embodiment of the present invention.

Referring to FIG. 19, the slider 36 is advanced relative to the control portion main body 34, the clip 26 is advanced relative to the sheath 28, the pressing member 40 is disposed at the distal end restricting position, the clip claw member 42 is advanced relative to the pressing member 40 to be disposed at the front end position, and the clip claw member 42 is opened to a maximum extent.

Figure 20:
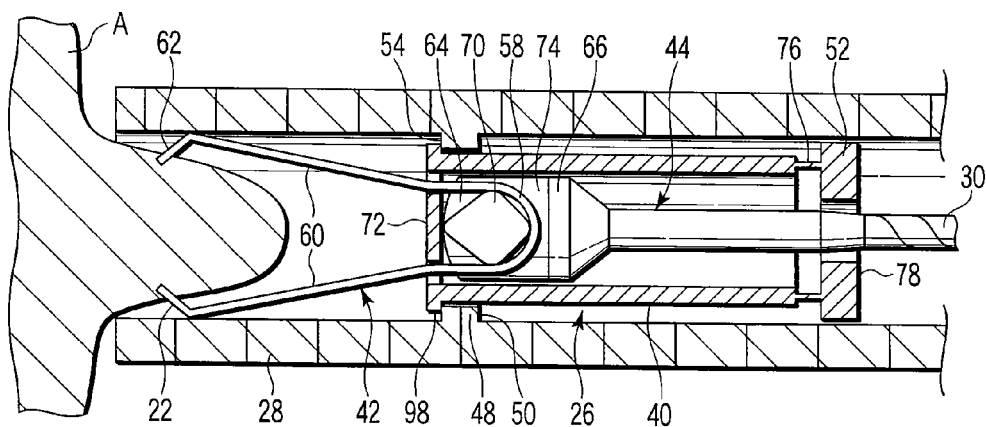
FIG. 20 is a longitudinal sectional view for explaining a step of temporal ligaturing in the ligaturing method using the ligation apparatus of the fifth embodiment of the present invention.

Referring to FIG. 20, after the distal end portion of the clip claw member 42 is pressed on the portion to be ligatured A, the slider 36 is retreated relative to the control portion main body 34. As a result, the clip 26 is retreated relative to the sheath 28, and the clip claw member 42 is closed by an inner peripheral wall of the sheath 28, so that the portion to be ligatured A is temporarily ligatured. Here, when the temporal ligature is not performed properly, re-ligaturing is performed. That is, the slider 36 is advanced relative to the control portion main body 34, the clip 26 is advanced relative to the sheath 28, and biasing to the clip claw member 42 imparted by the inner peripheral face of the sheath 28 is released, so that the clip claw member 42 is opened to release the portion to be ligatured A. Then, the temporary ligature is performed again.

Figure 21:
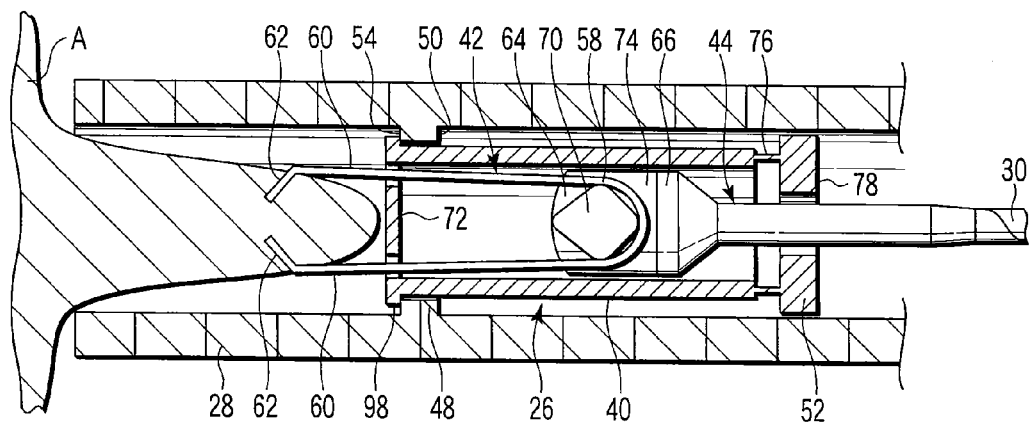
FIG. 21 is a longitudinal sectional view for explaining a step of primary ligaturing in the ligaturing method using the ligation apparatus of the fifth embodiment of the present invention.

Referring to FIG. 21, if the temporary ligature has been performed properly, transfer to a primary ligature is performed. That is, the slider 36 is retreated relative to the control portion main body 34, and the clip 26 is retreated relative to the sheath 28, so that the pressing member 40 is disposed at the rear end restricting position. Further, the slider 36 is retreated relative to the control portion main body 34, and the portion to be ligatured A is primarily ligatured like the first embodiment.

Figure 22:
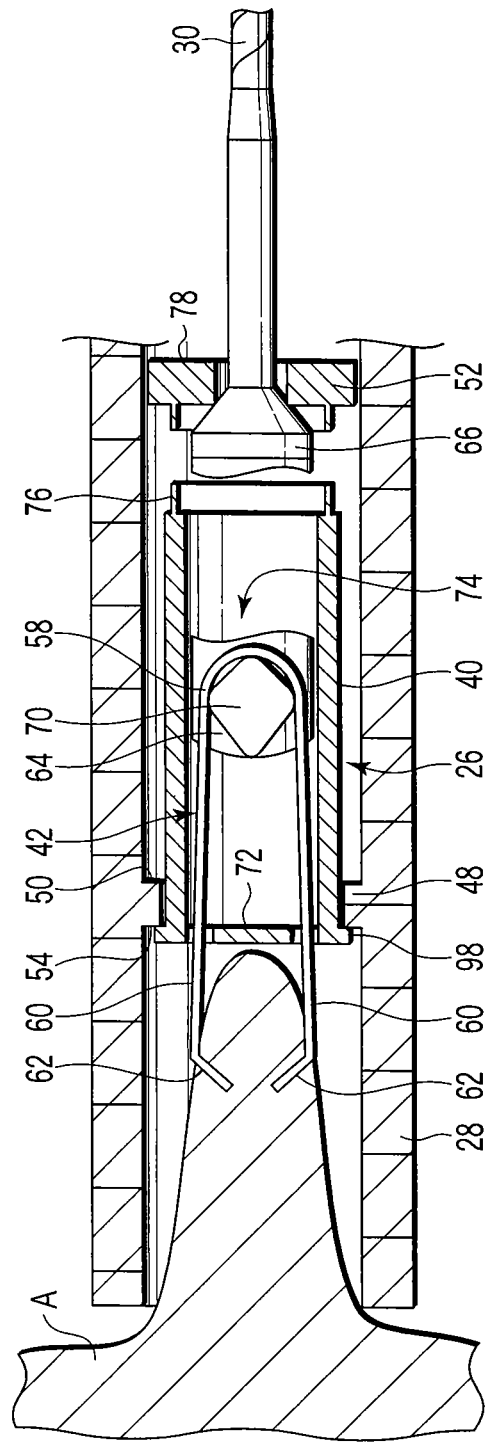
FIG. 22 is a longitudinal sectional view for explaining a step of separating a clip claw member and a pressing member in the ligaturing method using the ligation apparatus of the fifth embodiment of the present invention.
Figure 23:
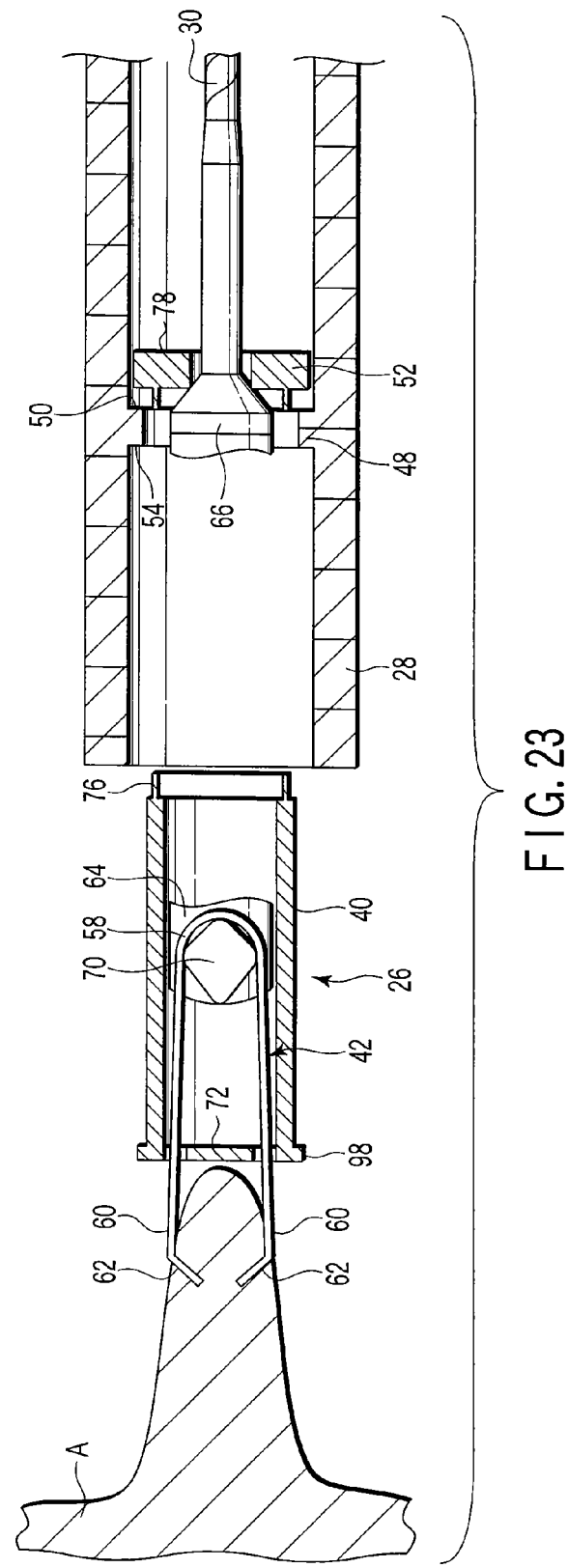
FIG. 23 is a longitudinal sectional view for explaining a step of releasing a clip in the ligaturing method using the ligation apparatus of the fifth embodiment of the present invention.

Referring to FIGS. 22 and 23, the clip claw member 42 is separated from the distal end portion of the operation wire 30 and the pressing member 40 is separated from the distal end portion of the sheath 28, and the clip 26 is separated from the distal end portion of the sheath 28 like the first embodiment.

Accordingly, the ligation apparatus of the embodiment achieves the following effect. When the elastically movable blade portions 56 are used as the retreat restricting mechanism for the pressing member 40 like the first embodiment, if such a state is maintained that the clip 26 is accommodated in the distal end portion of the sheath 28 and the blade portions 56 are folded in the pressing member 40, elasticity of the blade portions 56 degrade, which results in such a case that, when the pressing member 40 is protruded from the distal end portion of the sheath 28, the blade portions 56 are not expanded sufficiently and the function as the retreat restricting mechanism cannot be fulfilled sufficiently. In the embodiment, since a fixed retreat restricting large diameter portion 98 is used as the retreat restricting mechanism for the pressing member 40, such an event is avoided and retreat of the pressing member 40 can be restricted reliably.

Since, even after the clip 28 is separated from the distal end portion of the sheath 28, it is necessary to maintain such a state that the clip 28 has ligatured living tissue, a certain level of frictional force is required between the clip claw member 42 and the pressing member 40 such that the clip claw member 42 and the pressing member 40 are engaged with each other reliably. However, when the frictional force is excessively large, there is such a possibility that advance of the clip claw member 42 relative to the pressing member 40 is blocked and expanding of the clip claw member 42 is blocked. In the embodiment, in the temporary ligature that may be performed repeatedly, opening or closing of the clip claw member 42 is performed by advancing and retreating the clip 26 relative to the sheath 28, so that it is avoided that expanding of the clip claw member 42 is blocked by a frictional force between the clip claw member 42 and the pressing member 40.

The invention claimed is:

1. A ligation apparatus comprising:
   a sheath including a distal end portion and a central axis;
   a pressing member configured to engage with the distal end portion of the sheath and including a distal end and a proximal end;
   a clip claw member which is provided at the pressing member, which is configured to be advanced and retreated relative to the pressing member and which includes relatively openable and closable ends protruding from the distal end of the pressing member;
   an operation member inserted through the sheath, configured to be advanced and retreated relative to the sheath and including a distal end portion;
   a connection member connecting the distal end portion of the operation member and the clip claw member to each other; and
   an elastic member provided between the distal end and the proximal end of the pressing member configured to elastically deform based on the movement of an advance and a retreat of the elastic member along the central axis and configured to advance the clip claw member relative to the pressing member, the elastic member energizing the clip claw member so as to advance the clip claw member by an elastic deformation and so as to open the openable and closable ends of the clip claw member by an elastic force thereof, wherein the elastic member is provided separately from the clip claw member,
   wherein:
   the ligation apparatus is capable of re-grasping a living tissue a plurality of times at the openable and closable ends of the clip claw member,
   the ligation apparatus grasping living tissue by the clip claw member pulling in the pressing member to resist energizing force of the elastic member so as to close the openable and closable ends of the clip claw member when the operation member and the connection member are pulled backwards relative to the pressing member along the central axis of the sheath, and
   the ligation apparatus after grasping the living tissue by the openable and closable ends of the clip claw member, releasing the grasp of the living tissue with the clip claw member opening the openable and closable ends of the clip claw member protruded relative to the pressing member by an energizing force of the elastic member exerted when the pulling of the operation member and the connection member relative to the pressing member is released.

2. The ligation apparatus according to claim 1, wherein the elastic member is configured to produce a force for advancing the connection member relative to the pressing member.

3. The ligation apparatus according to claim 1, wherein the elastic member is a flat spring.

4. The ligation apparatus according to claim 1, wherein in the pressing member, a proximal end of the elastic member is on a further proximal side than the proximal end of the clip claw member.

5. The ligation apparatus according to claim 4, wherein the clip claw member is configured to be urged in a direction that the clip claw member expands in a radial direction and to open according to protrusion from the pressing member.

6. A ligation apparatus comprising: a sheath including a distal end portion and a central axis; a pressing member configured to engage with the distal end portion of the sheath and including a distal end and a proximal end; a clip claw member which is provided at the pressing member, which is configured to be advanced and retreated relative to the pressing member and which includes relatively openable and closable ends protruding from the distal end of the pressing member; an operation member inserted through the sheath, configured to be advanced and retreated relative to the sheath and including a distal end portion; a connection member connecting the distal end portion of the operation member and the clip claw member to each other; and an elastic member provided between the distal end and the proximal end of the pressing member, configured to elastically deform based on the movement of an advance and a retreat of the elastic member along the central axis and configured to advance the clip claw member relative to the pressing member, the elastic member energizing the clip claw member so as to advance the clip claw member by an elastic deformation and so as to open the openable and closable ends of the clip claw member by an elastic force thereof, wherein the elastic member is a coil spring, wherein: the ligation apparatus is capable of re-grasping a living tissue a plurality of times at the openable and closable ends of the clip claw member, the ligation apparatus grasping living tissue by the clip claw member pulling in the pressing member to resist energizing force of the elastic member so as to close the openable and closable ends of the clip claw member when the operation member and the connection member are pulled backwards relative to the pressing member along the central axis of the sheath, and the ligation apparatus after grasping the living tissue by the openable and closable ends of the clip claw member, releasing the grasp of the living tissue with the clip claw member opening the openable and closable ends of the clip claw member protruded relative to the pressing member by an energizing force of the elastic member exerted when the pulling of the operation member and the connection member relative to the pressing member is released.

* * * * *